United States Patent [19]
Bailey

[11] Patent Number: 5,094,615
[45] Date of Patent: Mar. 10, 1992

[54] DENTAL POLISHING HEAD AND METHOD
[75] Inventor: Ronald L. Bailey, Harvester, Mo.
[73] Assignee: Young Dental Manufacturing Company, Creve Coeur, Mo.
[21] Appl. No.: 477,748
[22] Filed: Feb. 9, 1990
[51] Int. Cl.⁵ .............................................. A61C 3/02
[52] U.S. Cl. ........................................ 433/88; 433/215
[58] Field of Search .................. 433/88, 80, 85, 84, 433/125; 51/410, 427, 436, 439; 222/566; 604/39

[56] References Cited
U.S. PATENT DOCUMENTS

| | | |
|---|---|---|
| 2,325,517 | 7/1943 | Howard . |
| 2,376,616 | 5/1945 | Oechsle ................................ 51/439 |
| 2,405,854 | 8/1946 | Ruemelin ............................. 51/438 |
| 3,690,061 | 9/1972 | Goss et al. ........................... 51/428 |
| 3,972,123 | 8/1976 | Black .................................. 433/88 |
| 4,174,571 | 11/1979 | Gallant ............................... 433/216 |
| 4,214,871 | 7/1980 | Arnold ................................ 433/88 |
| 4,253,610 | 3/1981 | Larkin ................................ 51/439 |
| 4,386,911 | 6/1983 | Maloney et al. .................... 433/125 |
| 4,412,402 | 1/1983 | Gallant ............................... 433/216 |
| 4,595,365 | 6/1986 | Edel et al. ........................... 433/88 |
| 4,676,749 | 6/1987 | Mabille .............................. 433/88 |
| 4,776,794 | 10/1988 | Meller ............................... 433/216 |
| 4,787,845 | 11/1988 | Valentine ........................... 433/88 |

Primary Examiner—Cary E. O'Connor
Attorney, Agent, or Firm—Polster, Lieder, Woodruff and Lucchesi

[57] ABSTRACT

A head or handpiece for a dental cleaner which cleans teeth by impinging soluble abrasive particles against teeth in the presence of a liquid. The head includes a gas/abrasive tube and a water tube which opens into an accumulator. The water is injected from the accumulator into the gas/abrasive tube through a hole therein. The water, air and abrasive combine in the air/abrasive tube to form a fine mist which exits through a nozzle. The exiting mist is formed to enable a hygienist to clean a small area of a tooth. A constant supply of bleed air flows through the gas/abrasive tube to force out remaining abrasive and fluid after the abrasive and fluid flow have been discontinued. A sleeve with a pair of bores through its sides is placed on the end of the nozzle to prevent water from backing up and clogging the head when the nozzle is pressed against a tooth.

25 Claims, 2 Drawing Sheets

DENTAL POLISHING HEAD AND METHOD

BACKGROUND OF THE INVENTION

This invention relates to the cleaning of teeth, and, in particular, to a head or handpiece for a cleaner which cleans by abrading a tooth surface with soluble abrasive particles in the presence of liquid. It is particularly directed to a device known to dentists and hygienists as an airpolisher. Airpolishers use air, abrasive, and liquid, combined in various ways, to clean and polish teeth, perform root planing, and reduce microbial count prior to oral surgery.

The use of a spray of soluble abrasive particles in the presence of a liquid to clean teeth has long been known. Several approaches have been used.

In some approaches, a stream of water in which abrasive is partially or completely dissolved is directed at the teeth. An example of such an approach is Arnold, U.S. Pat. No. 4,214,871. Although, as pointed out by Arnold, the use of liquid as the carrier for the soluble particles has the advantages over gas that it does not cool as it expands through a nozzle, that it has a residual flushing effect, and that the pressure does not have to be as great because of the higher density of liquids over gases, it is not an entirely effective way to clean and polish teeth. It also does not permit easy adjustment of the degree of cleaning performed.

Other approaches are exemplified by Gallant, U.S. Pat. Nos. 4,174,571 and 4,412,402. These patents use air as a carrier gas for the soluble abrasive; they direct the air/abrasive stream toward the tooth, and direct a separate stream of water toward the tooth.

In the former ('571) patent, the water stream is in the form of one or more jets arranged so that the water will impinge upon the surface being treated very close to or overlapping with the target area for the air/abrasive stream. When the water stream joins the air/abrasive stream, a slurry is formed and the cleaning or abrasion is effected, at least in part, by means of such slurry. Using this device, a hygienist must hold the head a certain distance from the tooth for the abrasive and water to properly mix at the tooth. Thus this cleaner is "technique sensitive." If the head is held too close to the tooth, the abrasive builds up in intradental spaces, reducing the effectiveness of the cleaner. Further, if the head is held still, the abrasive particles form a pile in the middle of the water curtain and the water flows around the abrasive pile. Thus, to clean the tooth effectively, the hygienist must continuously move the head in the patient's mouth at a fixed distance a few millimeters from the tooth surface. The device is therefore difficult to use for cleaning fine crevices or around orthodontal appliances. The device of the patent is also bulky and therefore difficult to use in the mouth of a patient. This drawback has been reduced somewhat in a commercial device made according to the patent, by forming a tip of concentric tubes. The device also requires a high air pressure which may cause discomfort to the patient and damage to soft tissue, such as gums, particularly if the nozzle is held directly against the tissue. It also produces a substantial aerosol overspray which may deposit throughout the operatory and is both an annoyance and a potential hazard.

In the latter ('402) patent, the discharge nozzle has a central orifice for the air/abrasive stream and an annular water orifice extending around and a short distance beyond the central orifice. Instead of delivering the water as a jet, the water is released as a non-pressurized flow and is caused to join (at least to some degree) the air/abrasive stream under the influence of the induction effect of the air/abrasive jet on the way to the tooth. Even though some of the abrasive may be dry when it impinges the tooth, no cloud of dry abrasive particles is produced because it is contained by the water curtain. Because mixing of the water with the air/abrasive stream occurs on the way to the tooth, the head must still be held a proper distance from the tooth, although it is somewhat less technique sensitive than the device of the '571 patent. Although this approach was intended to solve some of the problems of the '571 patent, it produced problems of its own, particularly clogging of the device. Clogging of the device may occur in normal operation, and causes major problems when the hygienist touches the nozzle to the patient's tooth or gum, thereby causing water to back up into the air/abrasive line. As a result, this device was not commercially successful.

Another approach is disclosed in Edel et al, U.S. Pat. No. 4,595,365. In this device, a pressurized air/abrasive stream and a pressurized water stream are mixed in a chamber in the head to provide a homogeneous mixture, and a single stream of this mixture exits the head. This approach has the virtue of being far less technique sensitive than the approaches of the Gallant patents. The head is bulky, however, because water is brought into the head from the side and because of the size of the mixing chamber. Moreover, the large volume and pressure of the water stream makes it difficult to control the correct air/abrasive/water mixture. It also produces a good deal of overspray in the patient's mouth and throughout the operatory. It also creates a potential problem of clogging, which becomes a very real problem should the hygienist accidentally block the outlet.

Yet another approach is shown in Meller, U.S. Pat. No. 4,776,794, in which a water/abrasive mixture is carried by a head and injected into an air stream. This approach requires a bulky head to carry the water/abrasive mixture, is not easily controlled, and requires the use of abrasive materials which are not readily soluble in water.

All of the prior art heads and methods also produce a spray which is not well focused and therefore are not well suited to cleaning small fissures or other small areas of a tooth or a root.

SUMMARY OF THE INVENTION

One of the objects of this invention is to provide a handpiece head for a dental cleaner which cleans teeth even more effectively than presently known cleaners.

Another object of this invention is to provide such a head and method which produces less aerosol overspray than presently known cleaners and is therefore neater, more convenient for the hygienist using it, more comfortable for the patient, and more sanitary.

Another object is to provide such a head which may focus on a very small area of a tooth.

Another object is to provide such a head which is simple to manipulate in a patient's mouth.

Another object is to provide such a head which requires very little water to clean effectively, but which wets the abrasive particles sufficiently to prevent the build-up of dry powder on the tooth and to leave a minimum of gritty residue in the patient's mouth.

Another object is to provide such a head which resists clogging in normal use and also when its nozzle is pressed against a tooth or tissue.

Another object is to provide such a head which minimizes erosion to the head by the abrasive.

Another object is to provide a head which cleans effectively independent of its distance, within a normal operating range of about one to five millimeters, from the tooth and without requiring movement with respect to the tooth.

Another object is to provide such a head which may be sterilized by autoclaving.

Other objects of this invention will be apparent to those skilled in the art in light of the following description and accompanying drawings.

In accordance with one aspect of this invention, generally stated, there is provided a dental cleaner having a handle, a head, a nozzle extending from the head, and a pair of tubes supplying abrasive laden gas and liquid to the head. Both the air/abrasive stream and the liquid stream are pressurized. In the head, the liquid supply tube opens into an accumulator which fills with liquid and overflows into the gas/abrasive tube. The abrasive supply tube continues through the head to form the nozzle. Preferably, the air/abrasive supply tube has a small hole therein which allows the liquid to enter the abrasive supply tube substantially at right angles to the axis of the supply tube. The hole is preferably rearward (upstream) of the end of the liquid supply tube.

In accordance with another aspect of the invention, a dental handpiece is provided comprising a first tube carrying a finely divided soluble abrasive in a gas and a parallel second tube carrying water. The first tube extends through the handpiece and forward thereof, and the second tube ends within the handpiece. Aperture means are provided in the first tube for injection of water from the second tube into the first tube in the form of a mist. Because most of the abrasive particles are wetted as the mist is formed, very little water need be injected into the particle stream. Thus, the water requirement is significantly reduced.

The liquid supply tube is smaller in diameter than the abrasive supply tube. Thus, the air/abrasive component is dominant and carries the liquid. This significantly reduces the amount of water that is needed to clean teeth and facilitates independent control of the amounts of water and abrasive which are carried to the tooth surface. An inner diameter of the air/abrasive supply tube of about 0.03" to 0.04" has been found desirable, in combination with an inner diameter of the water supply tube less than about 0.7 times that of the air/abrasive supply tube.

The water mist appears to perform several functions. The water droplets add substantially to the mass of the abrasive particles, increasing the mass of the abrasive particles several-fold. The water droplets appear to carry the abrasive particles, wetting them without dissolving them. Thus, as compared with a homogeneous slurry, the particles may maintain sharper edges and clean better. The water mist wets the particles sufficiently to prevent any pluming or build-up of dry abrasive.

The air/abrasive supply tube preferably has a small outer diameter, less than 0.06", is bent slightly, and extends from the head a substantial distance, over 0.5", to provide an easily maneuverable instrument for reaching difficult spots in the patient's mouth. The aperture in the air/abrasive supply tube through which the water is injected is preferably spaced from the tube's outlet by at least twenty times the inner diameter of the air/abrasive supply tube. The long, narrow tube carrying the air/abrasive/water mist provides a small, highly focused abrasive pattern on the tooth. It quickly cleans that small area, without requiring movement of the handpiece, and permits the hygienist to move without delay to another area. Because the mist impinges on a tooth in only a small area it reduces discomfort caused by abrasive impinging on the patient's gums. The small area of impingement becomes even more important during root planing to avoid abrading too much cementum and exposing the root. The device also produces less aerosol overspray than previously known airpolisher devices.

The tip of the nozzle is covered with a hollow cylindrical sleeve having a blow-by opening. The sleeve and opening prevent a back up of the liquid into the air/abrasive stream and consequent clogging when the nozzle is pressed against a tooth or tissue, but do not have any noticeable effect on the operation of the head during normal use.

The head has a continuous supply of bleed air flowing through the abrasive supply tube to prevent liquid from backing up into the abrasive tubes, thereby avoiding clogging at the head between uses.

Other aspects of the invention, including the methods of cleaning teeth using the techniques of the present invention, will be better understood in light of the following description of the preferred embodiment of the invention.

DESCRIPTION OF THE PREFERRED EMBODIMENT

Figure 1:
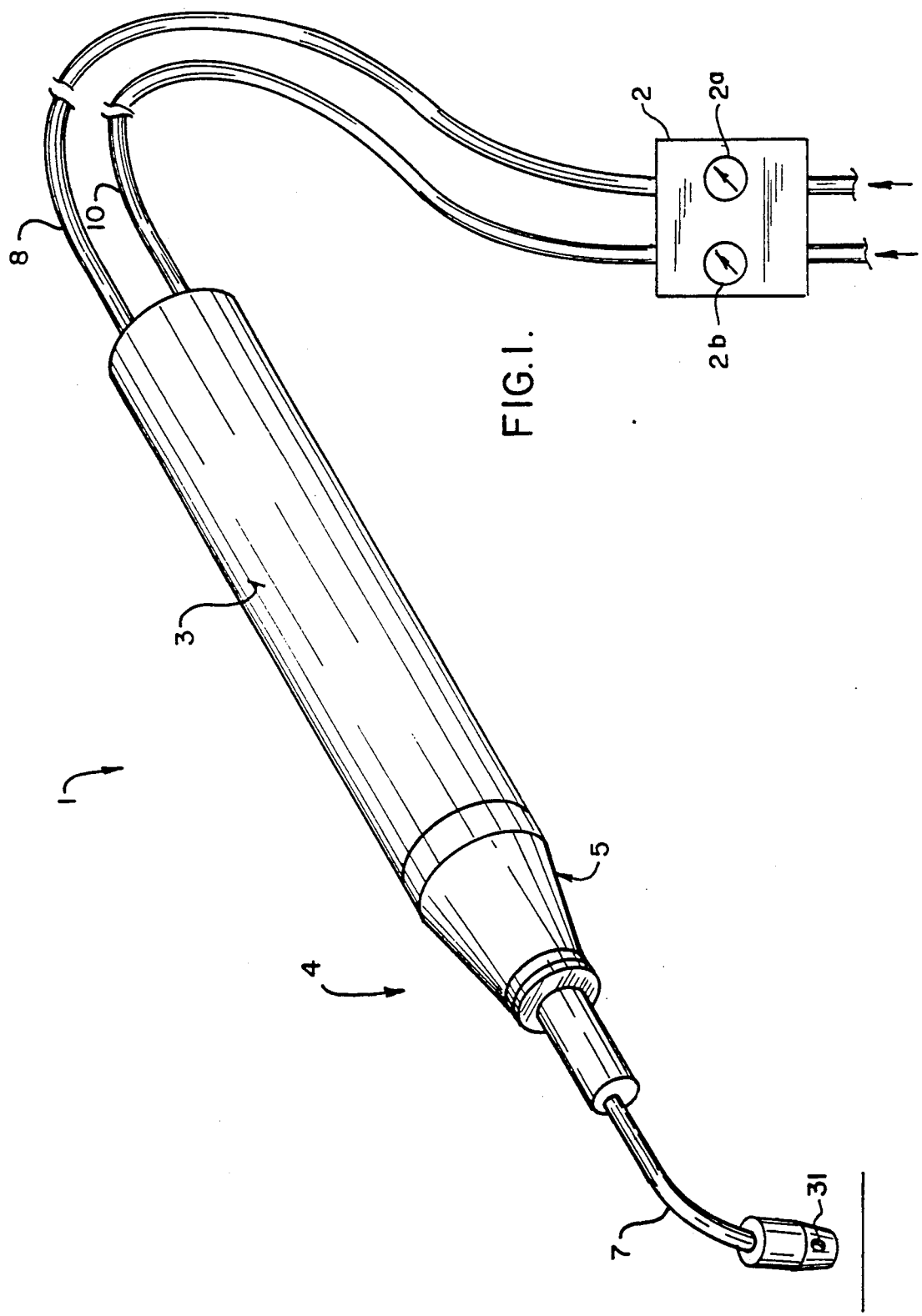
FIG. 1 is a perspective view of a dental airpolishing head or handpiece of the present invention, attached to a console unit.
Figure 2:
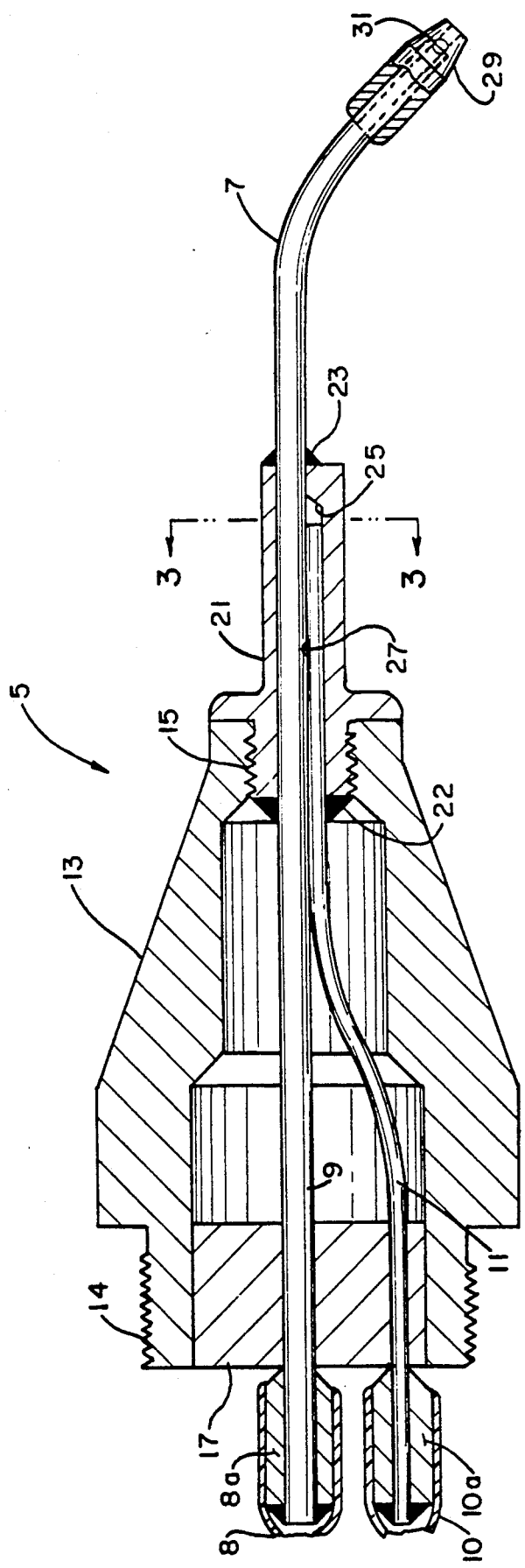
FIG. 2 is a cross-sectional view of the head of the tooth cleaner of FIG. 1.
Figure 3:
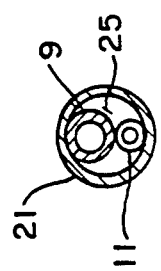
FIG. 3 is a cross-sectional view of the head taken along Line 3—3 of FIG. 2.
Figure 4:
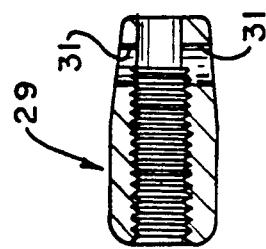
FIG. 4 in a cross-sectional view of a blow-by tip portion of the head of FIGS. 1-3.

Referring now to the drawings, reference numeral 1 indicates a dental airpolisher of the present invention. Airpolisher 1 includes a control box 2 and a handpiece 4 having a handle 3, a head 5, and a nozzle 7. The control box is preferably of a form described in my copending application, Ser. No. 477,609 filed Feb. 9, 1990. A pair of flexible tubes 8 and 10 connect the control box 2 with the rear of handle 3, where they are attached by adapters 8a and 10a, respectively. The adapter 8a is attached to a stainless steel tube 9, and the adapter 10a is attached to a stainless steel tube 11. The flexible tube 8 carries an abrasive-laden air stream to air/abrasive tube 9, and the flexible tube 10 carries a water stream to water tube 11. Both the air/abrasive stream and the water stream are pressurized. The water stream flows into handle 3 at approximately thirty psi; the air stream enters at approximately thirty psi. Both pressures are constant, even when the flow of abrasive and water is varied.

Head 5 comprises a housing 13 which is externally threaded at 14 to connect to handle 3. Housing 13 is also internally threaded at 15 to receive a hollow tube sleeve 21. Housing 13 is plugged at its rearward end by a spacer 17 and at its forward end by tube sleeve 21.

Spacer 17 supports tubes 9 and 11 in a spaced relation as they enter head 5. Air/abrasive tube 9 continues straight through head 5 and tube sleeve 21 to form nozzle 7. The abrasive thus flows in a substantially straight path, the path having only a gentle, approximately thirty degree bend near the center of nozzle 7. This reduces the tendency of abrasive to erode the interior of the head, and extends its useful life.

Water tube 11 bends gently within head 5 to a position parallel to and tangentially adjacent air/abrasive tube 9 before entering sleeve 21. Water tube 11 terminates in an open end near the forward, downstream, end of sleeve 21. Sleeve 21 is soldered at 22 to form a seal around the tubes 9 and 11 at the entry of sleeve 21; it is soldered at 23 to form a seal around the tube 9 at the exit of sleeve 21. The interior diameter of the sleeve 21 is equal to the sum of the outer diameters of the tubes 9 and 11. The interior of sleeve 21 forms an accumulator 25 within sleeve 21. A small metering hole 27 in air/abrasive tube 9 allows water to enter air/abrasive tube 9 from accumulator 25. Hole 27 is positioned at the tangential junction of tubes 9 and 11, rearward of the end of tube 11.

Accumulator 25 serves two purpose. First, it serves as a reservoir to constantly supply water to the air/abrasive tube as will be described below. Secondly, it serves to dampen the effects of the water velocity as it exits tube 11.

Air/abrasive tube 9 preferably has a larger diameter than water tube 11. An air/abrasive tube with an inner diameter of 0.034" (outer diameter 0.050") in combination with a water tube having an inner diameter of 0.020" (outer diameter 0.032") has been found to produce a focused mist, as explained above. When the tubes are of equal size, for example 0.036", it has been found that too much water enters the air/abrasive tube 9. The excess water in the air/abrasive tube limits the ability of the air to pick up the abrasive from its source and can result in nearly shutting off the abrasive flow. To further restrict the flow of water into the air/abrasive tube, hole 27 is made very small, preferably between 0.016" and 0.018" in diameter. The distance between hole 27 and the end of nozzle 7 is 0.925", and the portion of the tube 9 forming nozzle 7 extends beyond the end of the head 5 about 0.625".

In operation, the hygienist picks up the handpiece 4, positions the nozzle 7 in a patient's mouth, then activates control box 2 by means of a foot pedal, not shown. The foot pedal preferably operates sequentially through a first stage and a second stage when depressed, then back through the first stage when released.

The first stage is a rinse mode in which water and air, without abrasive, are simultaneously brought through flexible tubes 8 and 10 to the handpiece 4. The water fills accumulator 25. The water pressure in tube 11 and accumulator 25 injects the water in accumulator 25 into air/abrasive tube 9 through hole 27, substantially at right angles to the flow of air and abrasive. The water spray extends about halfway into tube 9 before it is picked up by the air/abrasive stream. A mist of air and water droplets is sprayed from the nozzle 7 onto the patient's teeth. The first stage is arranged to increase water pressure and deliver more water than would normally pass through the nozzle 7 for a quicker rinse.

As the foot pedal is depressed to the second stage, the air picks up an amount of abrasive set by a control knob 2a on the control box 2. When the air/abrasive stream meets the water spray injected into tube 9, a fine mist is formed. The amount of water can also be adjusted by a control knob 2b on the control box. The mist exits nozzle 7 in a focused pattern. The water droplets attach to the particles in the air/abrasive stream and increase the effective mass of the particles several-fold. The increased effective mass of the particles reduces the air pressure required for effective cleaning. Because the water emanating from the nozzle is in the form of a mist of fine droplets carrying the abrasive particles, rather than as a stream forming a curtain around dry particles, effective cleaning can be obtained with very little water.

Hole 27 effectively meters the flow of water into air/abrasive tube 9, and thus assures that the air/abrasive stream is dominant. With the air stream dominant, water entering tube 9 does not detrimentally affect abrasive pick-up and there is not sufficient water present to dissolve the abrasive particles. Thus, the integrity of the abrasive particles is maintained and there is sufficient abrasive to effectively clean teeth.

In the mist, all or most of the particles are wetted, even though very little water is used. The particles are not sufficiently wetted to dissolve them. Thus, the abrasive particles maintain their effectiveness as cleaners, and there is very little aerosol cloud formation. Therefore, a majority of the particles act as cleaners.

Because the abrasive particles are attached to fine droplets of water, and because the mist impinging on the patient's teeth is focused to a narrow spot, the air-polisher of the present invention produces far less aerosol overspray or plume than do previously known air-polishers. Because the abrasive is wetted, a hygienist can clean a single spot without having to move the head to wash away piles of abrasive.

When the control is released, it passes through the first, rinse, stage. Again, air without abrasive is passed through the tube 9, while water is passed through tube 11. Abrasive is cleared from the tube 9 by the air and water spray, and the possibility of clogging is reduced.

To sterilize the handpiece, the handle 3 is unscrewed from the head 5, the flexible tubes 8 and 10 are removed from the adapters 8a and 10a, the handle is slipped off of the tubes 8 and 10, and the handle and head are sterilized in an autoclave before being replaced.

To prevent the tubes from backing up and clogging the head when the nozzle is pressed against a tooth, gum, or other tissue, nozzle 7 has a hollow blow-by sleeve 29 placed thereon. Sleeve 29 includes a pair of bores 31 which are aligned on sleeve 29 such that they are partially closed by the end of nozzle 7. Blow-by sleeve bores 31 serve to relieve pressure in the head when nozzle 7 is pressed against a tooth or tissue, thereby preventing water from backing up into air/abrasive tube 9 and clogging the head. The blow-by sleeve 29 also prevents tissue emphysema. A maximum pressure of nine psi has been recorded when the tip is sealed against a surface. This is not enough pressure to inject air into a tissue.

The inner diameter of sleeve 29 is preferably 0.046", slightly larger then the 0.034" inner diameter of the nozzle. Bores 31 have a diameter of 0.035". Thus the combined diameter of the bores (0.070") is greater then the inner diameter of the sleeve 29 and the exit mist does not spray through bores 31 when the nozzle is placed against the tooth, rather, it tends to "gurgle". Sleeve 29 does not affect the shape of the mist which exits nozzle 7.

To prevent clogging of the head 5 between uses, the head is supplied with a constant flow of bleed air. The bleed air will force abrasive and water out of nozzle 7 after the flow of abrasive and water is discontinued to help keep the head from clogging. Any abrasive that may remain and dry within nozzle 7 is not sufficient to clog head 5, and when the cleaner is used the next time, the mist removes this dried abrasive. Thus, the head is self-cleaning. The bleed air also helps in preventing water from backing up into the air/abrasive tube 9.

Numerous variations, within the scope of the appended claims, will be apparent to those skilled in the art in light of the foregoing description and accompanying drawings. Merely by way of example, the geometries and dimensions of the parts may be varied. The preferred abrasive is a commercially available soluble sodium bicarbonate powder formulated for use in air-polishers and having a particle size in the range of about 140 to 200 mesh. Such powder may have flow enhancers and flavorants added. Nonetheless, other particulate abrasives which are at least partially soluble in the operating liquid may be used. The preferred operating liquid is water, but other liquids may be used. The metering orifice in the tube 9 may be formed as a plurality of smaller holes. The blow-by tip may provide other passages than a cross-bore for relieving pressure when the tip is sealed against a surface. These variations are merely illustrative.

I claim:

1. A dental cleaner for cleaning teeth with soluble abrasive particles in the presence of a liquid, said cleaner comprising a handle, a head on said handle, a nozzle extending from said head, and a pair of tubes supplying an abrasive laden gas and a liquid to said head, wherein, said liquid and said abrasive laden gas are under pressure;

said liquid supply tube opens into an accumulator within said head, said liquid filling said accumulator;

said abrasive laden gas supply tube having an opening to said accumulator, said liquid being injected into said abrasive laden gas supply tube to form a mist of gas, abrasive particles and liquid in said abrasive laden gas supply tube;

said mist exiting said head through said nozzle; and said nozzle being a continuation of said abrasive laden gas supply tube.

2. The cleaner of claim 1, wherein said abrasive laden gas supply tube opening is rearward of the opening of said liquid supply tube to said accumulator.

3. The cleaner of claim 2, wherein the liquid pressure in said liquid supply tube and in said accumulator injects said liquid into said abrasive laden gas supply tube.

4. The cleaner of claim 1, wherein said nozzle has a blow-by tip on the end thereof, said tip including aperture means for preventing the backup of liquid into said abrasive laden gas stream when the nozzle is pressed against a tooth.

5. The cleaner of claim 1, wherein the liquid supply tube has a smaller diameter than the abrasive laden gas supply tube.

6. The cleaner of claim 5 wherein the liquid supply tube has an inner diameter of less than 0.7 times the diameter of the abrasive laden gas supply tube, the abrasive laden gas supply tube having an inner diameter of from 0.03" to 0.04".

7. The cleaner of claim 5, wherein the opening in the abrasive laden gas supply tube is a hole in the wall of the abrasive laden gas supply tube, the hole having an area of less than 0.0003 square inches.

8. The cleaner of claim 7, wherein said hole is round and is 0.016" to 0.018" in diameter.

9. The cleaner of claim 1, including a source of bleed air running through the abrasive laden gas supply tube whenever the cleaner is activated to prevent liquid from backing up into the abrasive laden gas supply tube.

10. In a dental cleaner which cleans by impinging soluble abrasive particles on a tooth in the presence of a liquid, the cleaner comprising a handle, a head on the handle, abrasive carrying means for carrying abrasive to the head, liquid carrying means for carrying liquid to the head, and nozzle means on the head, said nozzle means having an outlet, the improvement comprising blow-by means on said nozzle means for relieving pressure in said nozzle means when said outlet of said nozzle means is held against a surface, said blow-by means being spaced upstream from said outlet.

11. The improvement of claim 10 wherein both liquid and abrasive are carried to said nozzle outlet, and wherein said blow-by means prevents liquid from backing up into said abrasive carrying means and consequent clogging of said head.

12. The improvement of claim 11, wherein said blow-by means comprises a sleeve which cooperates with the end of said nozzle means.

13. The improvement of claim 12, wherein said sleeve includes at least one bore through the side thereof providing an exit for said abrasive and liquid when said outlet is placed against said surface.

14. The improvement of claim 10, wherein said outlet has a smooth, unbroken periphery, and said blow-by means comprises aperture means closely adjacent said outlet.

15. A method for effecting abrasion of a tooth surface comprising directing a stream of air and soluble abrasive particles toward the surface through a nozzle; filling a reservoir with liquid, said liquid entering said reservoir from a liquid tube; and metering said liquid through a metering opening into the stream before the stream exits the nozzle whereby the stream of air and soluble abrasive is dominant over the liquid, the metering opening having an effective area smaller than the cross-sectional area of the liquid tube; the liquid particles wetting substantially all of the abrasive particles and increasing their mass several-fold before they are ejected from the nozzle.

16. The method of claim 15 wherein the nozzle is a tube, and including a step, after injecting the mist of liquid into the stream, of conducting the mist of liquid and particles through the tube a distance at least twenty times the diameter of the tube.

17. A dental handpiece comprising a first tube carrying a finely divided soluble abrasive in a gas and a second tube carrying water, the first tube and second tube being parallel, the first tube extending through the handpiece and forward thereof, the second tube ending within the handpiece, and aperture means in the first tube for injection of water from the second tube into the first tube in the form of a mist.

18. The handpiece of claim 17 wherein the aperture means has an area of less than 0.0003 square inches.

19. A dental cleaner for cleaning teeth with soluble abrasive particles in the presence of a liquid, said cleaner comprising a handle; a head on said handle; a nozzle extending from said head; a tube supplying an abrasive laden gas to said nozzle; a liquid supplying tube; a reservoir in communication with said liquid supplying tube so that said liquid supplying tube feeds into said reservoir, said reservoir being in fluid communication with said abrasive laden gas supplying tube; and means for maintaining the abrasive laden gas dominant over the liquid.

20. The dental cleaner of claim 19 wherein said maintaining means comprises a metering opening in said reservoir defining an exit from said reservoir to said abrasive laden gas supply tube upstream of said nozzle.

21. The dental cleaner of claim 20 wherein said liquid supplying tube has a diameter substantially smaller than said abrasive laden gas tube.

22. A dental cleaner for cleaning teeth with soluble abrasive particles, air and water, said cleaner comprising a source of a stream of air and soluble abrasive particles; a source of water; a handle; a head on said handle; a nozzle tube extending from said head; a first tube connecting said source of air and abrasive particles to said head; a second tube connecting said source of water to said head; aperture means in said head for introducing said water into said stream of air and soluble abrasive particles in the form of droplets which wet the soluble abrasive particles without dissolving the particles; and a nozzle tube having a substantially uniform diameter, said nozzle tube extending from said aperture means to an outlet a distance of at least about twenty times the inner diameter of the nozzle tube.

23. The cleaner of claim 22 wherein the nozzle tube has an outer diameter less than 0.06" and extends from the head over 0.5", to provide an easily maneuverable instrument for reaching difficult spots in a patient's mouth.

24. The cleaner of claim 22 comprising an air/abrasive tube within said head, said air/abrasive tube connecting said first tube and said nozzle tube, said air/abrasive tube having the same inner diameter as said nozzle tube.

25. The cleaner of claim 24 wherein said air/abrasive tube is integral with said nozzle tube.

* * * * *